(12) United States Patent
Clemente et al.

(10) Patent No.: US 12,230,901 B2
(45) Date of Patent: Feb. 18, 2025

(54) ANTENNA DEVICE FOR NEAR-FIELD ILLUMINATION OF THE SKIN BY MILLIMETRE WAVES

(71) Applicant: Commissariat à l'énergie atomique et aux énergies alternatives, Paris (FR)

(72) Inventors: Antonio Clemente, Grenoble (FR); Maciej Smierzchalski, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 192 days.

(21) Appl. No.: 17/805,476

(22) Filed: Jun. 6, 2022

(65) Prior Publication Data

US 2022/0393358 A1 Dec. 8, 2022

(30) Foreign Application Priority Data

Jun. 7, 2021 (FR) ..................................... 21 05960

(51) Int. Cl.
*H01Q 9/04* (2006.01)
*A61B 5/0507* (2021.01)
(Continued)

(52) U.S. Cl.
CPC ......... *H01Q 9/0464* (2013.01); *A61B 5/0507* (2013.01); *A61N 5/02* (2013.01); *H01Q 1/42* (2013.01); *H01Q 1/48* (2013.01)

(58) Field of Classification Search
CPC .......... H01Q 9/0464; H01Q 1/42; H01Q 1/48; A61B 5/0507; A61N 5/02; H04B 5/72; H04B 5/26
See application file for complete search history.

(56) References Cited

U.S. PATENT DOCUMENTS 6,184,828 B1 2/2001 Shoki
11,128,059 B2 * 9/2021 Rogers ................. H01Q 9/0428
(Continued)

FOREIGN PATENT DOCUMENTS

WO WO 2019/053290 A1 3/2019

OTHER PUBLICATIONS

French Preliminary Search Report issued Feb. 24, 2022 in French Application 21 05960 filed on Jun. 7, 2021, 3 pages (with English Translation of Categories of Cited Documents).
(Continued)

*Primary Examiner* — Awat M Salih
(74) *Attorney, Agent, or Firm* — Oblon, McClelland, Maier & Neustadt, L.L.P.

(57) ABSTRACT

The invention relates to an antenna device configured to superimpose a plurality of electromagnetic modes in the near field, with a multilayer structure comprising, in a vertical stacking direction:
 a first power supply layer comprising a first dielectric on an application-specific integrated circuit and on a lower part of a DC power supply circuit,
 a second power supply layer comprising an upper part of a DC power supply circuit,
 a third layer comprising a second dielectric on a metal plane,
 a fourth layer comprising at least one planar radiating element, the metal plane acting as a grounding plane,
 a fifth layer comprising a radome,
the antenna device comprising at least one feed line extending from the first to the fourth layer.

13 Claims, 8 Drawing Sheets

(51) Int. Cl.
*A61N 5/02* (2006.01)
*H01Q 1/42* (2006.01)
*H01Q 1/48* (2006.01)

(56) References Cited

U.S. PATENT DOCUMENTS

2018/0301807 A1* 10/2018 Clemente ................ H01Q 3/34
2021/0091463 A1* 3/2021 Shahvirdi Dizaj Yekan ...............
                                                      H01Q 3/36
2021/0194512 A1* 6/2021 Clemente ............. H04B 1/0064

OTHER PUBLICATIONS

Smierzchalski, "Characterization methods for metamaterials. Directive antennas using space eigen-modes.", Universite De Rennes 1, ANNEE 2014, 279 pages.

* cited by examiner

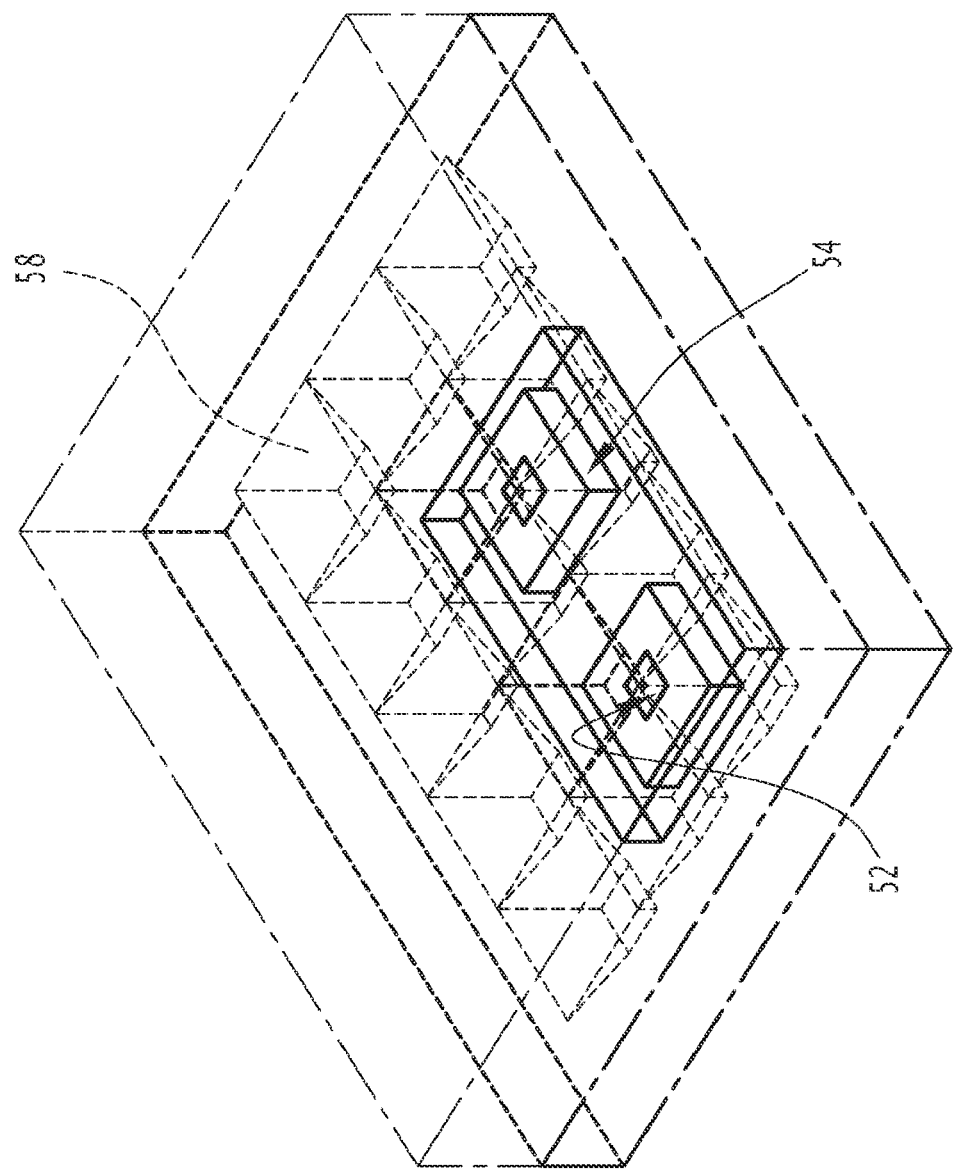

ANTENNA DEVICE FOR NEAR-FIELD ILLUMINATION OF THE SKIN BY MILLIMETRE WAVES

CROSS-REFERENCE TO RELATED APPLICATIONS

This application is a U.S. non-provisional application claiming the benefit of French Application No. 21 05960, filed on Jun. 7, 2021, which is incorporated herein by reference in its entirety.

FIELD

The present invention relates to an antenna device for near-field illumination of the skin by millimetric waves.

The invention lies in the field of near-field focused antenna systems useful in a large number of applications, in particular for radars dedicated to medical applications and medical devices based on electromagnetic waves and radio frequencies. These medical devices are suitable for use in diagnosis (detection of cancer, stroke, etc.) or also for treatment and therapy (stimulation of endorphins, cancer therapy, therapy of bone fractures, etc.)

BACKGROUND

Microwave-based techniques are generally non-invasive, but require innovative antenna solutions to cope with the high penetration losses due to the presence of skin and other inhomogeneous media. More generally, in the case of radar systems for medical applications, near-field focused antenna technologies are suitable for use in increasing the transfer and/or focusing capacities of electromagnetic energy in inhomogeneous media (human tissues or on the surface of the skin, stratified media, etc.)

In the state of the art, antennas focused in the near field are known, in particular for application in future communication systems associated with sixth-generation communication networks which also require reconfigurable intelligent surfaces capable of operating in the near field to adjust and best manage the characteristics of the electromagnetic waves involved and dynamically control the propagation channel.

For medical applications, near-field focused antennas are known, such as a simple horn antenna as a near-field source, or even more recent mobile devices for millimeter wave therapy whose frequency is below 300 GHz, using an antenna network such as the device described in the document WO 3071 163 A1 where the network uses a supply network of T-junctions which mixes the layers of RF radio frequency and direct current (DC) signals. However, the solution according to document WO 3071 163 A1 presents losses and in particular requires four specialized integrated circuits ASIC (application-specific integrated circuit) of 20 mW.

SUMMARY

The object of the invention is to remedy the drawbacks of the state of the art by proposing an alternative near-field antenna architecture for the uniform and punctual illumination of the skin, suitable for reducing losses as well as the number of ASIC(s) necessary for its power supply and the associated cost, while remaining nevertheless compact. In other words, the aim of the invention is to propose an alternative antenna architecture capable of generating a specific electromagnetic field distribution, in amplitude or in amplitude and in phase, on or in a stratified and inhomogeneous medium (i.e. in a specific plane located at a defined distance from the radiating aperture and on a specific layer of the stratified medium).

To this end, the invention proposes an antenna device for near-field illumination of the skin by millimeter waves in which said device is configured to superimpose a plurality of electromagnetic modes in the near field, using a multilayer structure comprising, in one direction vertical stacking:
- a first power supply layer including at least a first dielectric on an integrated circuit for specific application and on a first lower part of a metallic DC power supply circuit,
- a second DC power supply layer, superimposed on the first power supply layer in the vertical stacking direction, and including a second upper part of a metal DC power supply circuit,
- a third layer, superimposed on the second supply layer in the vertical stacking direction, and including a second dielectric on a metal plane,
- a fourth layer comprising at least one planar radiating element of said antenna device, the fourth layer being superimposed on the third layer in the vertical stacking direction, the metal plane of the third layer acting as the ground plane of the element radiant, and
- a fifth layer, superimposed on the fourth layer in the vertical stacking direction, and including a radome capable of separating said at least one radiating element from the skin,
- the antenna device further including at least one feed line extending vertically from the first layer to the fourth layer.

Advantageously, the architecture (i.e. the stack) of the proposed antenna device for near-field illumination of the skin by millimeter waves is thus, once powered and activated, configured to superimpose a plurality of electromagnetic modes and to minimize losses via the metal plane of the third layer, which also acts as the ground plane of the radiating element.

In other words, according to the present invention, the proposed antenna device combines in the near field region a linear combination of a series of radiating modes to satisfy the particular radiation distribution requirements, each mode being excited in a specific manner in amplitude and in phase, by means of said architecture, to correctly construct the required field distribution.

The antenna device for near-field illumination of the skin by millimeter waves can also have one or more of the characteristics below, taken independently or according to all technically possible combinations:
- the electromagnetic modes capable of being superimposed are cylindrical modes;
- said, at least one planar radiating element is a fleeing wave radiating element corresponding to at least one patch with annular slot(s), or to at least one patch with continuous transverse stubs being known by the acronym CTS (continuous transverse stub) or else according to one of the names "network of continuous transverse stubs", or "networks with continuous transverse stub";
- the third layer comprises at least one transverse row of metal via(s) defined by the vertical stacking direction and a transverse direction perpendicular to the vertical stacking direction, said at least one transverse row of metal via(s) extending vertically from the metal ground plane of the third layer to the plane of the fourth layer comprising at least one planar radiating element;

said at least one planar radiating element is a fleeing wave radiating element corresponding to at least one patch with annular slot(s), the third layer comprising, on either side of said at least one patch with annular slot(s), at least one transverse row of metal via(s) extending vertically from the metal ground plane to the plane of the fourth layer comprising said at least one patch with annular slot(s), said at least one feed line extending vertically from the centre of the first feed layer to the centre of said at least one patch with annular slot(s);

said at least one planar radiating element is a fleeing wave radiating element corresponding to at least one patch with continuous transverse stubs, the third layer comprising, on either side of said at least one patch with continuous transverse stubs, at least one transverse row of metal via(s) extending vertically from the metal ground plane to the plane of the fourth layer comprising said at least one patch with continuous transverse stubs, said at least one supply line extending vertically from the centre of the first layer to the centre of the fourth layer comprising said at least one patch with continuous transverse stubs, the slots of said at least one patch with continuous transverse stubs being distributed symmetrically on either side of the feed point provided by the feed line within the fourth layer;

said at least one planar radiating element is a fleeing wave radiating element corresponding to at least one patch with continuous transverse stubs, the third layer comprising, located substantially close to a first transverse end of said third layer, at least one transverse row of metal via(s) extending vertically from the metal ground plane to the plane of the fourth layer comprising said at least one patch with continuous transverse stubs, said at least one supply line, extending vertically from the first layer to the fourth layer being via(s) located at the level of a second transverse end, of the third layer, parallel and opposite to the first transverse end of said third layer located substantially close to said at least one transverse row of metal via(s), said at least one supply line being able to excite the first magnetic transverse mode tick of said at least one patch with continuous transverse stubs;

the device further comprises between said at least one transverse row of metal via(s) and said at least one supply line at least two other metal via(s) extending vertically from the metal ground plane to the plane of the fourth layer comprising said at least one patch with continuous transverse stubs;

said at least one planar radiating element is a fleeing wave radiating element corresponding to at least one patch with continuous transverse stubs, the third layer comprising, located substantially close to a first transverse end of said third layer, at least one transverse row of metal via(s) extending vertically from the metal ground plane to the plane of the fourth layer comprising at least one patch with continuous transverse stubs, and comprising at least two longitudinal waveguides obtained by insertion at the within the third layer of at least one other longitudinal perpendicular row of metal via(s), in a longitudinal direction, both to said at least one transverse row of metal via(s) and to the metal ground plane, said at least one other longitudinal row of metal via(s) extending vertically from the metal ground plane to the plane of the fourth layer comprising at least one patch with continuous transverse stubs;

said at least one longitudinal row of metal via(s) extends longitudinally from said at least one transverse row of metal via(s) and beyond the last slot of said at least one patch with continuous transverse stubs while stopping at a distance from a second transverse end, of the third layer, parallel and opposite to the first transverse end of said third layer, located substantially close to said at least one transverse row of metal via(s), at least one supply line, extending vertically from the first layer to the fourth layer, being located longitudinally between:

the end of said at least one longitudinal row of metal via(s) opposite to at least one transverse row of metal via(s), and the second transverse end of the third layer, parallel and opposite the first transverse end of the third layer located substantially close to said at least one transverse row of metal via(s); and said at least one longitudinal row of metal via(s) extends longitudinally from it at least one transverse row of metal via(s) and beyond the second transverse end, of the third layer, parallel and opposite the first transverse end of said third layer located substantially close to said at least one transverse row of metal via(s), the antenna device then comprising at least two feed lines, extending vertically from the first layer to the fourth layer, being located transversely on either side of said at least one longitudinal row of metal via(s);

the electromagnetic modes capable of being superimposed further comprise comprising cavity modes capable of being excited by adding at least one metal cavity within the multilayer structure; and the radome being configured to be a modulated dielectric blanket.

BRIEF DESCRIPTION OF THE DRAWINGS

These characteristic features and advantages of the invention will emerge from the description given below, by way of indication and in no way limiting, with reference to the appended figures, among which are:

FIG. 8 illustrates an alternative embodiment in which the radome is configured to be a modulated dielectric blanket.

DETAILED DESCRIPTION

Figure 1:
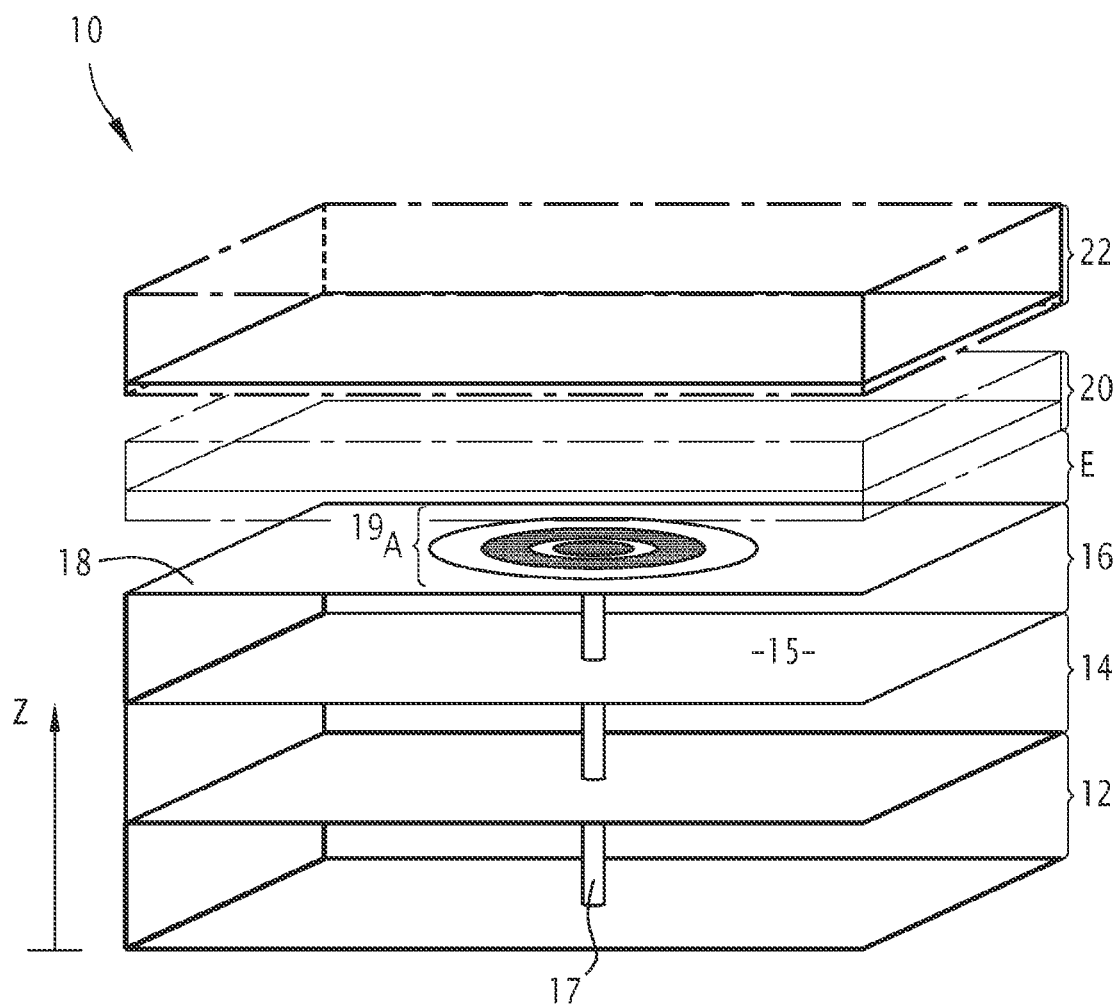
FIG. 1 schematically represents the architecture of the antenna device for near-field illumination of the skin by millimeter waves according to a first embodiment.

FIG. 1 schematically represents the general architecture of the antenna device 10 for near-field illumination of the skin for millimetric wave therapy according to the present invention.

The general configuration of such a device 10 is based on a compact multilayer structure comprising in particular at least one RF radiofrequency element, a power supply system, an antenna source, a radome (i.e., in particular a plastic cover) separating the device antenna 10 from the skin and a skin model, the device 10 operating in the reactive zone of the antenna.

More specifically, according to the present invention, the compact multilayer structure of the antenna device 10 comprises, in a vertical stacking direction Z, firstly includes a first supply layer 12 including a first dielectric on an integrated circuit for specific ASIC application (application-specific integrated circuit) and a first lower part of the DC power supply metal circuit. In other words, the first layer 12 includes a first dielectric substrate resting on the lower face on a metallization comprising the ASIC as well as on a first lower part of the metallic DC power supply circuit, as illustrated subsequently by FIG. 3.

The radiofrequency output power of the ASIC of the first layer 12 is in particular 20 mW, capable of providing a minimum power flux of 50 W/m2 to obtain interaction with the skin by illumination of more than 95% of its surface approximately.

In addition, the compact multilayer structure of the antenna device 10 further includes a second DC power supply metal layer, superimposed on the substrate of the first power supply layer 12 in the vertical stacking direction Z, and including, so that the upper face of the substrate of the layer 12 includes a second upper part of the metallic DC power supply circuit.

Moreover, the compact multilayer structure of the antenna device 10 of FIG. 1 further includes a third layer 16, superimposed on the second metallic supply layer in the vertical stacking direction Z, and includes a second dielectric on a metallic plane 15.

Furthermore, the antenna device 10 further includes at least one direct feed metal line 17 extending vertically from the first layer 12 to a fourth layer 18 comprising at least one planar radiating metal element $19_A$ of said antenna device 10, the fourth layer 18 being superposed on third layer 16 in the vertical stacking direction z, metal plane 15 of third layer 16 acting as the ground plane of radiating element $19_A$.

More specifically, according to a particular variant, on the second metal layer including the upper part of the direct current power supply is also superimposed a preimpregnated film 14 (prepeg) making it possible to secure the substrate of the first layer 12 by bonding to that of the third layer 16 in order to optimize the use of their respective metal planes. In other words, the stack of layers 12, 14, 16 and 18 according to the present invention includes according to this variant two dielectric substrates of layers 12 and 16 and five distinct levels of metallization corresponding respectively to the ASIC, at the two lower and upper levels direct current power supply metal circuit located vertically on either side of the substrate of layer 12, to the metal plane 15, and to said at least one radiating element $19_A$.

According to another variant, the layer 14 corresponds to an additional layer of substrate allowing the use of alternative bonding techniques to the prepreg such as a bonding of the high temperature type, or a sintering of ceramics at low temperature (Low temperature co-fired ceramic).

In other words, the stack of layers 12, 14 and 16 through which the said at least one power supply line 17 extends vertically is dedicated to the supply of the RF radiofrequency layer 18, and responsible for the distribution of the power to said at least one radiating element $19_A$. Such a power supply corresponds for example to a serial or parallel power supply implemented according to different production techniques such as the T-junctions of the strip lines or the propagation waves associated with waveguides integrated into each SIW substrate (Substrate Integrated Waveguide).

According to a particular aspect, in the presence of a pre-impregnated bonding film within the layer 14, capable of producing a ground discontinuity, to optimize the transition between the ASIC of the first layer 12 and the power supply line 17, whose base is equivalent to a coaxial, and ensure continuity of the mass, coupling studs (coupling stub) not shown in FIG. 1, and illustrated later in FIG. 3 (with the metal vias 30 of layer 12), are suitable for insertion around supply line 17 to implement this transition.

The fourth layer 18 of radiation is responsible for the excitation of the fields in the reactive zone E corresponding to a free space above the layer 18 comprising at least one planar radiating element. As detailed below, the radiating element of the fourth layer 18 corresponds, for example, to an array of patches, and in particular using one or more slot(s) to generate a given order mode in the reactive zone, or even one or more cavity modes.

In addition, the compact multilayer structure of the antenna device 10 of FIG. 1 further comprises a fifth layer 20, superimposed on the fourth radiation layer 18 and from which it is vertically separated by a space E, in the vertical stacking direction Z, and comprising a radome capable of separating said at least one radiating element from the skin illustrated by the layer 22 of FIG. 1.

Alternatively, space E is able to be replaced by a bonding film.

Between the skin 22 and the radiation layer 18, such a cover layer 20, in particular made of plastic and for example 2 mm thick, is used according to the present invention to isolate the human body from the radiation system corresponding to the antenna device 10. Indeed, for medical reasons, skin 22 cannot directly touch the metal parts of the antenna device 10. Moreover, if the skin 22 is wet, the presence of such a covering layer 20 is suitable for avoiding degrading the performance of the antenna device 10.

The fifth layer 20, treated as a semi-finished matching medium and bounded by the skin and the radiation layer 18, has a crucial impact on the power distribution on the skin 22 in the reactive spot.

According to a particular optional aspect, the fifth layer 20 is also able to present a gradual index change.

Thus, the upper layers, 16, 18 and 20 of radiation and coverage make it possible to design the RF radiative part of the antenna device 10, while the lower metal layers on either side of the layer 12 are used for the routing of the direct current and RF transceiver integration in circuit terms.

Compared to the antenna device described in document WO 3071 163 A1, based on a T-junction feed system and a patch antenna, where there is a strong mutual coupling between the RF and DC layers, the metal plane 15, introduced according to the present invention to play the roles of separation between the upper part RF composed of layers 16, 18 and 20, and the lower part composed of layers 12 of supply and 14 of connection, and to play the role of plane mass of said at least one radiating element $19_A$ allows a reduction of the mutual coupling between the RF and DC layers and a minimization of losses.

The skin layer 22 of FIG. 1, modeling the skin, corresponds to a known skin model associated with an equivalent permittivity, a conductivity and a loss tangent at a given frequency. Such parameters are also suitable for taking into account the different levels of moisture concentration in the skin.

Advantageously, as described in more detail later in relation to FIG. 3, the antenna device 10 has a size of 10×10 mm$^2$ and only requires a source ASIC of 20 mW whereas the current antenna devices for illumination in field near the skin by millimetric waves, in particular the antenna device described in the document WO 3071 163 A1 require a greater number of ASICs of 20 mW.

According to a particular aspect illustrated by FIGS. 2 to 5, said at least one planar radiating element of the fourth layer 18 is a radiating element with receding waves corresponding to at least one patch with annular slot(s) 19$_A$ or at least one less a patch with continuous transverse stubs 19$_B$ or even a circular patch, a ring or any other radiating element with receding waves.

Said at least one "patch with continuous transverse stubs" is known by the acronym CTS (continuous transverse stub) or according to one of the names "network of continuous transverse stubs", or "networks with continuous transverse stub".

A leaky wave radiating element has the advantage of being compatible with the antenna device architecture 10 proposed according to the present invention based, as indicated previously, on a separation between the upper layers 16, 18 of radiation and 20 of coverage allowing to design the RF radiative part of the antenna device 10, and the lower layers 12 and 14 used for the routing of the direct current and the integration of the RF transceiver in terms of circuit, and this with five distinct levels of corresponding metallization respectively to the ASIC, to the two lower and upper metal DC supply circuits both dedicated to the power division, to the metal plane 15, and to the said at least one radiating element 19$_A$ or even 19$_B$.

More specifically, a leaky wave radiating element is a single-layer structure in terms of substrate (i.e., the layer (i.e., the plane) 18 of radiating element resting on the third layer 16 of dielectric substrate of FIG. 1) requiring no dividing complex power source but usually a serial power supply. The appropriate modulation or the use of higher order cylindrical modes of this type of radiating element, advantageously makes it possible to effectively distribute the near field and to minimize losses.

In particular, the radiation of such a leaky wave radiating element is obtained by the transition from a surface wave (i.e., stationary wave) to a leaky wave, which makes it possible to reduce the dimensions of the wave radiating element. The physical phenomenon that governs the near field distribution is based on the superposition of modes in the reactive area/near field. In fact, the higher order modes launched in the medium between the skin and the antenna device 10 are capable of being superimposed in a constructive manner when they are excited with a predetermined amplitude and phase.

According to a particular aspect of the present invention, the electromagnetic modes capable of being superimposed are cylindrical modes, the cylindrical modes having the simplest analytical model for the summation of the modes.

Figure 2:
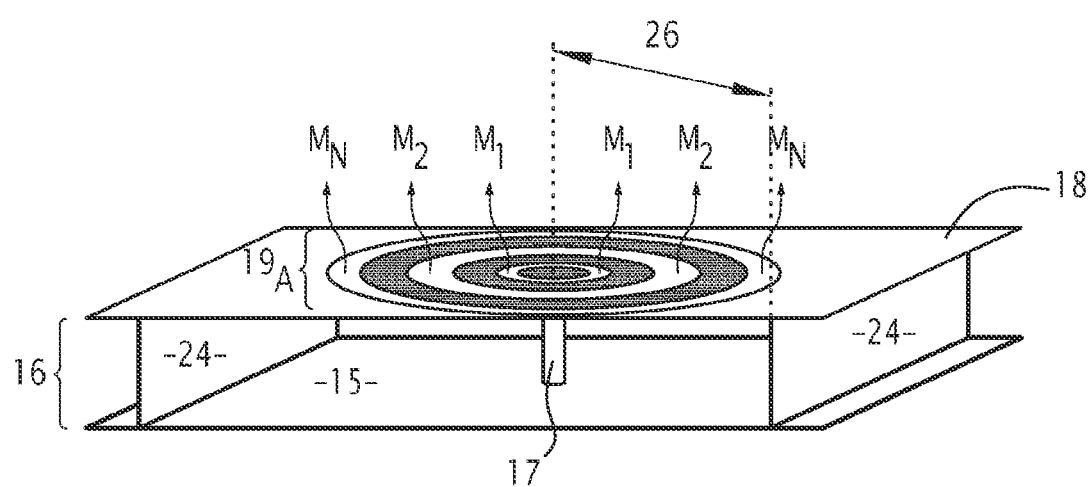
FIGS. 2 and 3 illustrate in perspective and in section such an architecture in which the planar radiating element is a radiating element with receding waves corresponding to a patch with annular slot(s)

In particular, when the leaky wave radiating element corresponds to a circular patch, a ring or a patch with annular slots 19$_A$ as illustrated by FIG. 2, the higher order cylindrical modes capable of being superimposed according to the present invention depend on the radius of the radiating element, and for a ring the radius and the size of the ring define the radiated mode number.

As illustrated by FIG. 2, the fleeing wave radiating element, corresponding in particular to a patch with annular slot(s) 19$_A$, is excited in series by the aforementioned central power supply 17 which circulates a wave in the dielectric substrate of the third layer 16 illustrated by FIG. 1, so as to generate a quasi-uniform or multi-spot distribution of the near field inside the traveling wave feeding the concentric network of annular slots of size and defined position of the patch with annular slot(s) 19$_A$.

Cylindrical modes are conventionally defined by a source of vector electric and/or magnetic potentials with a uniquely azimuthal periodic variation and the elementary cylindrical wave function is conventionally expressed in the following form:

$$\gamma_{k_\rho,n} = H_n^{(2)} e^{-jk_\rho\rho} \begin{Bmatrix} \sin n\varphi \\ \cos n\varphi \end{Bmatrix} \rightarrow \frac{j^n e^{-jk_\rho\rho}}{\sqrt{\rho}} \begin{Bmatrix} \sin n\varphi \\ \cos n\varphi \end{Bmatrix}$$

where n is the order of the mode, the other variables being defined by M. Smierzchalski within the document entitled "*Characterization methods for metamaterials. Directive antennas using space eigenmodes*" Univ. Rennes 1, 2014. The field radiated by the cylindrical modes is proportional to the electric (or magnetic) vector potential A=$\hat{z}\gamma_{k_\rho,n}$ and consequently to the cos nφ distribution. The realization of the variation in cosine of the fields is possible by a circular distribution of the current with use of an annular or split ring as illustrated by FIG. 2.

The superposition of the cylindrical modes for the multi-spot near field and the uniform distribution of the power density on the skin implemented according to the present invention assumes that each cylindrical mode is excited with an amplitude $a_n$ and a given phase $\varphi_n$.

In the synthesis of near-field and far-field radiation, a total electric vector potential for N cylindrical modes such as $A_{total} \approx \Sigma_{n=1}^N a_n \cos(n\varphi + \varphi_n)$ is in particular suitable for use.

Moreover, an appropriate set of amplitude and phase of the cylindrical modes selected beforehand, makes it possible to generate a pencil beam, a conical beam or any other form of beam pattern.

As illustrated by FIG. 2, each slot of the patch with annular slot(s) 19$_A$ with N slots in the infinite ground plane 15 generates a particular cylindrical mode $M_1$, $M_2$, $M_N$ respectively determined by its radius.

A serial power supply makes it possible to use a single excitation 17 which simultaneously supplies the N modes and makes it possible to avoid the use of a parallel or serial power supply network with N excitation nodes which is complex to implement. and associated with losses.

As illustrated by FIG. 2, according to a particular aspect of the present invention, the third layer 16 comprises at least one transverse row 24 of metal via(s) defined by the vertical stacking direction z and a direction perpendicular to the vertical stacking direction, with at least one transverse row of metal via(s) extending vertically from the metal ground plane 15 of the third layer 16 to the plane of the fourth layer 18 comprising at least one radiating element 19$_A$.

Such a row 24 of metal via(s) makes it possible to produce a metal wall, such a metal wall being, as an alternative, capable of being produced by continuous metallization instead of said discontinuous row 24 of metal via(s).

In comparison, a conventional stray wave radiator is open at the transverse ends of the third layer 16 and the traveling wave (or surface wave) attenuated by approximately −20 dB before reaching the edge of the third layer 16, which leads the radius (i.e., the dimension) of the conventional leaky wave radiating element to several wavelengths, and makes it bulky. In particular, such an attenuation of 20 dB on the edge conventionally requires an antenna radius of several wavelengths, which at 60 GHz can correspond to a radius of the order of 25 mm.

The presence of said at least one transverse row 24 of metal via(s) proposed according to this particular aspect of the present invention advantageously makes it possible to considerably reduce the size of the antenna while creating, on the one hand, a stationary wave at a given frequency, leading to a narrow band solution, and limiting on the other hand, the number of periods of the modulated surface and the performances in the far field (low gain and high sidelobe) and in the near field (focusing of the beam).

However, for the application of near-field illumination of the skin targeted by the present invention, the effects associated with such an advantageous reduction in size have no impact on the proposed application. Indeed, the antenna device 10 proposed according to the present invention for millimetric therapy can be narrowband since it operates at 62.25 GHz in a passband of 1.6%. Additionally, the small size of the antenna is required in such a mobile application where a focusing beam for deep skin penetration is required.

Thus, in FIG. 2, the array of cylindrical slots of the fleeing wave radiating element corresponding to a patch with annular slot(s) 19A is printed on the dielectric substrate of the third layer 16 grounded via the ground plane 15 and short-circuited on each transverse edge by said at least one row 24 of metal via(s). The coaxial pin 17 feeds the leaky wave radiating element corresponding to a patch of annular slot(s) 19A at the centre of its origin, triggering the first mode of electromagnetic propagation TM01 in the parallel plate waveguide. Part of the wave energy is lost through the slits and part propagates. In the event that all the energy is not evacuated by the slots, the progressive wave is reflected by the short-circuited edge by means of said at least one row 24 of metal via(s) creating a reflection back and therefore a stationary wave. The retro-reflected wave also hits the slit and leaks through the slot.

In other words, according to the embodiment of FIG. 2, said at least one planar radiating element is a fleeing wave radiating element corresponding to at least one patch with annular slot(s), the third layer 16 comprising, either side of said at least one patch with annular slot(s) $19_A$, where at least one transverse row of metal via(s) 24 extending vertically from the metallic ground plane to the plane of the fourth layer 18 including at least one patch with annular slot(s), and at least one supply line 17 extending vertically from the centre of the first supply layer 12 of FIG. 1 to the centre of said at least a patch with annular slot(s) $19_A$.

Thus, according to the present invention, for a constructive summation of the two leakage waves, the position of the short-circuit via each row 24 of metal via(s) in particular materialized at the distance 26, and the position of the slots of the leaky wave radiating element of the antenna device 10 are defined beforehand so that the antenna device 10 is properly configured to superimpose a plurality of electromagnetic modes in the near field. Such a preliminary definition is obtained in particular by optimising the summation ((i.e., superposition) of the electromagnetic modes radiated in the near field by means of simulations in particular via the three-dimensional simulation tool HFSS®.

Figure 3:
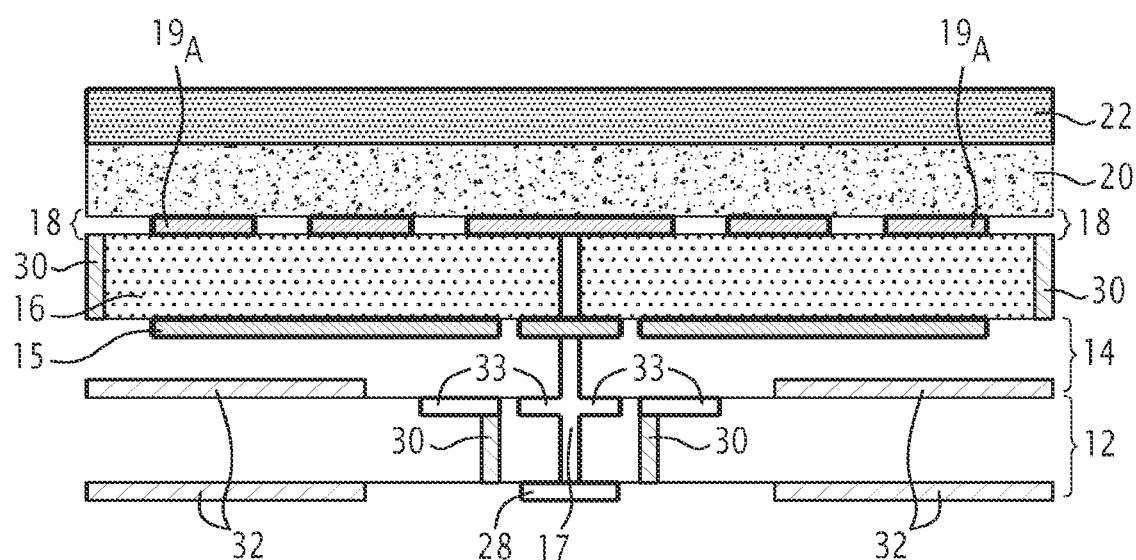

FIG. 3 illustrates a sectional view of a modeling via the three-dimensional simulation tool HFSS® of an antenna device 10 according to the present invention, such an antenna device 10 comprising a cylindrical leaky-wave antenna illuminating the skin.

As detailed previously in relation to FIG. 1, such an HFSS simulation model of the antenna device 10 according to the present invention comprises the stacking of layers 12, 14, 16, 18, 20 and 22 previously described.

Figure 4:
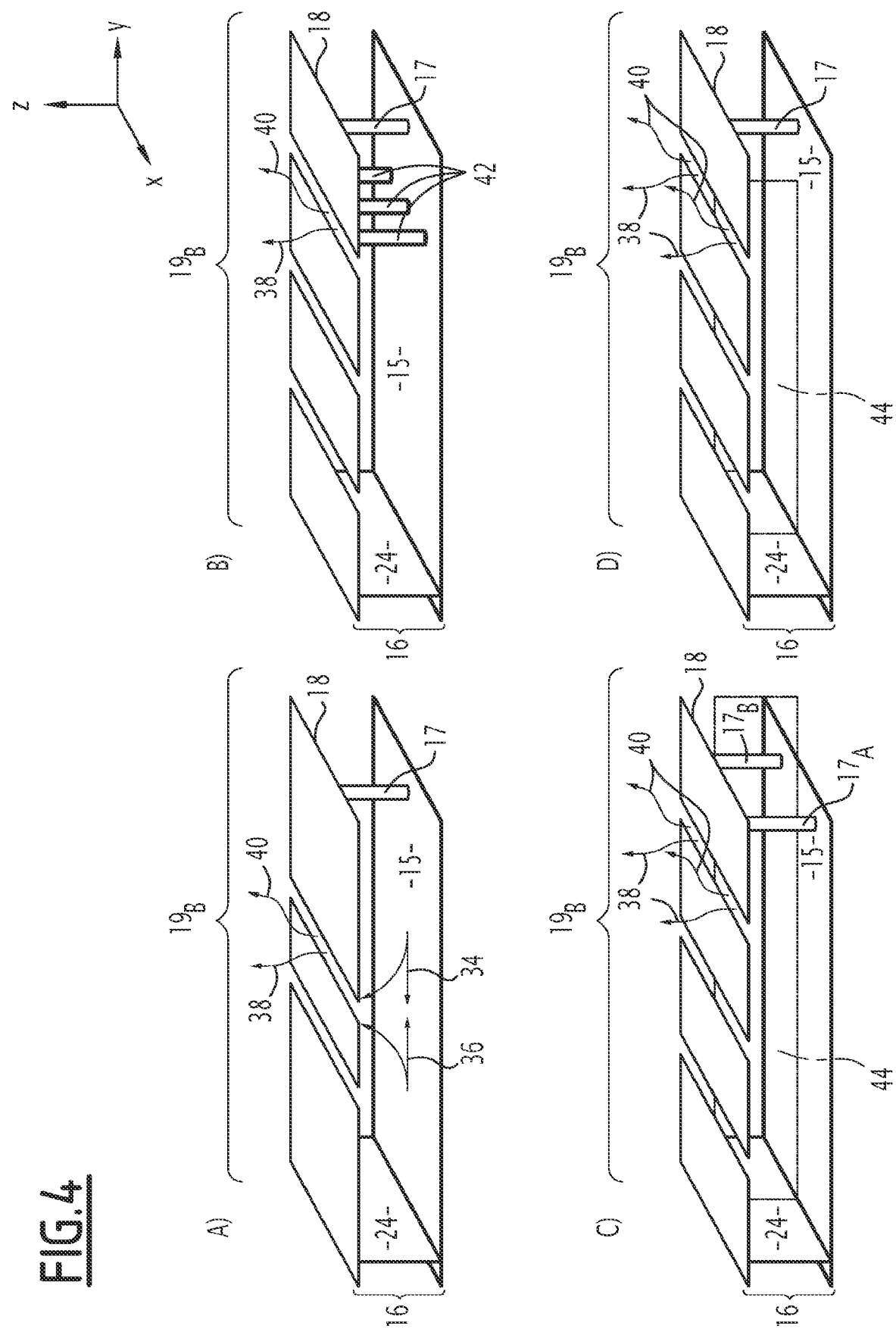
FIGS. 4 and 5 illustrate in perspective different variants of the proposed architecture in which the planar radiating element is a radiating element with at least one patch with continuous transverse stubs.
Figure 5:
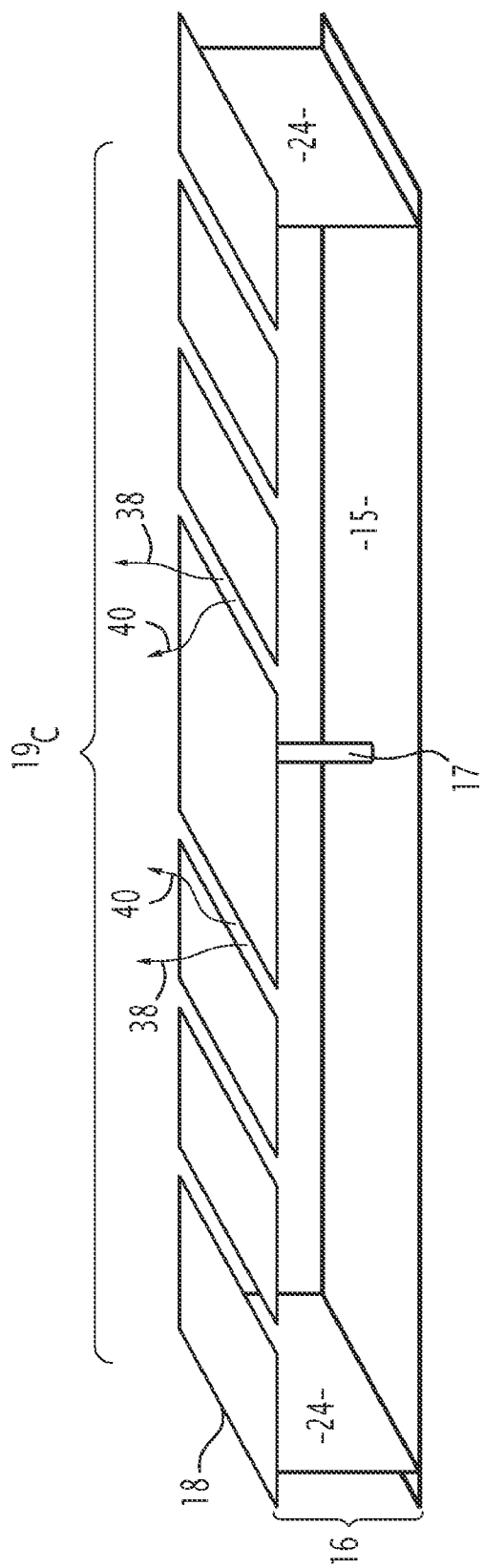

The waveguide with parallel plates, corresponding to the metallisations of the metallic ground plane 15 and to the metallisations of the planar radiating element, corresponding in FIG. 3 to a patch with annular slot(s) $19_A$, or to a patch with continuous transverse stubs $19_B$ as illustrated subsequently by FIGS. 4 and 5, is supplied directly by the RF radio frequency output of ASIC 28, located under the substrate of layer 12, via the coaxial supply pin 17. The dielectric layer 20 between the skin and the antenna is necessary to allow the superposition of the cylindrical modes in the near field. Short-circuits are made by metal vias 30, in particular, the metal vias 30 of layer 16 correspond to said at least one transverse row 24 of metal via(s) previously defined in relation to FIG. 2, and the metal vias 30 of the layer 12 correspond to short circuits making it possible to link the two supply layers 12 and 14.

The two layers of the DC direct current power supply circuit correspond to metallisations 32 located vertically on either side of the substrate of layer 12 necessary for the DC direct current power supply and coupling pads 33 (coupling stub) to ensure ground continuity and compensate for the presence of a preimpregnated connecting film 14 capable of producing ground discontinuity, such ground continuity making it possible to optimize the transition between the ASIC 28 of the first layer 12 and the feed line 17, whose base is equivalent to a coaxial.

As illustrated by FIG. 3, the cylindrical mode antenna as such requires only two metal levels $19_A$ (or $19_B$) for the radiating slot(s) and 15 for the separating ground plane, the antenna layer 16, metal feed layers of layer 12 including ASIC 28 and two layers of lower and upper metal levels 32 used for DC power circuits.

For example, a radiating surface of 10 mm×10 mm is adapted for using a three annular slot patch $19_A$.

FIG. 4 illustrates different variants A), B), C), D) of the invention where the radiating element with fleeing waves corresponds to a patch with continuous transverse stubs $19_B$.

In particular according to variant A), the patch with continuous transverse stubs $19_B$ of the plane 18 rests on the third layer 16 including, located substantially close to a first transverse end of the said third layer 16, at least one transverse row of metal via(s) 24 (i.e. along the x direction) extending vertically (along the z direction) from the metal ground plane 15 to the plane of the fourth layer 18 comprising said at least one patch with continuous transverse stubs $19_B$, said at least one supply line 17, extending vertically from the first layer 12 illustrated by FIGS. 1 and 3 to the fourth layer 18, being substantially located at the level of a second transverse end, of the third layer 16, parallel and opposite the first transverse end of said third layer 16 located substantially close to said at least one transverse row of metal via(s) 24, said at least one line of a power supply 17 being able to excite the first transverse magnetic mode TM01 of said at least one patch with continuous transverse stubs $19_B$.

In other words, the antenna device 10 corresponds according to variant A to a network of cylindrical slots short-circuited on one of these transverse edges (in the direction x) by at least one transverse row of metal via(s) 24.

More precisely, the TM01 mode, launched within the antenna (formed of layers 16 and 18), excites according to the arrows 34 each slot inside the antenna with a given amplitude and phase. This TM01 mode driven by power pin 17 creates a leaky cylindrical wave on each slot. This wave is reflected along the arrows 36 by the short-circuited wall on the edge of the parallel plate waveguide opposite said power supply 17, and creates a reflected wave. Thus on each slot we see two excited and reflected waves respectively creating dominant 38 and reflected 40 radiating modes. The sum of these two modes defines the cylindrical modes superimposed in the near field and thus concentrated in the reactive zone for treatment of the skin by the antenna device 10 according to this variant A.

The variants B), C) and D) of FIG. 4 aim to exploit the properties of the superposition of N first dominant modes by also using the progressive or standing wave as the serial supply of the slots and aim at more compact applications than that associated with variant A).

Taking into account the first N modes in the summation ((i.e., superposition) of electromagnetic modes obtained by means of the antenna device 10 according to the present invention, makes it possible to simplify the design of the antenna (formed of layers 16 and 18). Indeed, under the assumption of a single-mode type summation, there is no relationship with the slit radius and the whole design depends on the position and size of the slits (equivalent to phase and amplitude).

Variant B) is similar to variant A) previously described except that the patch with continuous transverse stubs $19_B$ comprises three slots instead of two according to variant A) and that the third layer 16 further includes, between said at least one transverse row of metal via(s) 24 and said at least one supply line 17, at least two other metal vias 42 extending vertically from the metal ground plane 15 to the plane of the fourth layer 18 comprising said at least one patch with continuous transverse stubs $19_B$.

In other words, for a more compact application than that targeted according to variant A), variant B) introduces a second transverse metal wall formed from said at least two other metal vias 42.

Moreover, compared to the variant of FIG. 5 described below, the use of metal vias 42 also makes it possible to apply a transformation of the cylindrical wavefront into a plane wavefront, and to obtain a uniformity of the phase and of the radiating fields.

The use of the metallized vias 42 is suitable for limiting the possibility of formation of a plane wave at a higher frequency than that desired and the variants C) and D) based on the use of two waveguide sections are proposed according to the present invention to remedy this.

In other words, in both variants C) and D), said at least one planar radiating element is a fleeing wave radiating element corresponding to at least one patch with continuous transverse stubs $19_B$, the third layer 16 comprising, located substantially near a first transverse end of said third layer 16, at least one transverse row of metal via(s) 24 (in the x direction) extending vertically (in the z direction) from the metal ground plane 15 to the plane of the fourth layer 18 including at least one patch with continuous transverse stubs $19_B$, and comprising at least two longitudinal waveguides (in the direction y of FIG. 4) obtained by insertion within the third layer 16 at least one other longitudinal row of metal via(s) 44 perpendicular, in a longitudinal direction y of FIG. 4, both to said at least one transverse row of metal via(s) 24 (according to direction x) and to the metal ground plane 15, said at least one other longitudinal row of metal via(s) 44 extending vertically (in the direction z) from the metal ground plane 15 to the plane of the fourth layer 18 including said at least one patch with continuous transverse stubs $19_B$.

According to variant C), said at least one longitudinal row of metal via(s) 44 extend(s) longitudinally, along y, from said at least one transverse row of metal via(s) 24, and beyond the second transverse end of the third layer 16, parallel to and opposite the first transverse end of said third layer 16 located substantially close to said at least one transverse row of metal via(s) 24, the antenna device 10 then comprising at least two supply lines 17A and $17_B$, extending vertically from the first layer 12 to the fourth layer 18 being located transversely on either side of said at least one row of metal via(s).

According to variant D), said at least one longitudinal row of metal via(s) 44 extends longitudinally, along y, from said at least one transverse row of metal via(s) 24 and beyond the last slot of said at least one patch with continuous transverse stubs $19_B$ while stopping at a distance from a second transverse end, of the third layer, parallel and opposite to the first transverse end of said third layer located substantially close to said at least one transverse row of metal via(s) 24, said at least one supply line 17, extending vertically, along z, from the first layer 12 to the fourth layer 18 being located longitudinally, along y, between:

the end of said at least one longitudinal row of metal via(s) 44 opposite to said at least one transverse row of metal via(s) 24, and the second transverse end, of the third layer, parallel to and opposite the first transverse end of said third layer located substantially close to said at least one transverse row of metal via(s) 24.

In other words, variant figures C) and D) show long slots fed by two waveguide sections driven by two and only one pin 17 respectively.

FIG. 5 shows an alternative variant of FIG. 2 where instead of a patch with annular slots $19_A$, said at least one planar radiating element is a radiating element with fleeing waves corresponding to at least one patch with continuous transverse stubs $19_B$, the third layer 16 comprising, on either side of said at least one patch with continuous transverse stubs, at least one transverse row of metal via(s) extending vertically from the metallic ground plane to the plane of the fourth layer comprising said at least one continuous cross section patch, said at least one supply line extending vertically from the centre of the first layer to the centre of the fourth layer comprising said at least one continuous cross section patch, the slits of said at least one patch with continuous transverse stubs being distributed symmetrically on either side of the feed point supplied by the feed line 17 within the fourth layer.

This alternative of FIG. 5 thus has short circuits 24 on the transverse edges to allow its use in compact applications. In addition, a single power supply per pin 17 is applied. In the proposed structure of FIG. 5, the propagation of the excited TM01 mode in the parallel plate waveguide extends in all directions. Leakage waves with a phase difference of 180° when the slots are symmetrical with respect to the feed point of the feed line 17 are then obtained, as well as a dominant mode 38 and a reflected mode 40 in the reactive zone due to the presence of short circuits 24.

Due to the short-circuiting wall 24 on one of the edges, the dominant and reflected TM01 mode radiates in the reactive zone but presents a cylindrical wave front, which creates a phase delay on the slots and non-uniform radiation.

To remedy this, the variants B), C) and D) previously described, and as verified in particular by simulation, also make it possible to apply a transformation of the cylindrical wavefront into a plane wavefront with respect to the variant of FIG. 5, to achieve phase uniformity and superimposed radiant fields which creates a near-uniform power distribution across the skin, and to provide effective illumination of the skin with almost twice weaker power consumption.

According to an aspect not represented, the combination ((i.e., superposition) of the modes is further able to be carried out electronically in order to produce an electron beam formation in the near field region. For example, this combination can be implemented by parasitic load elements with adjustable components such as capacitors, resistors and/or inductors.

Figure 6:
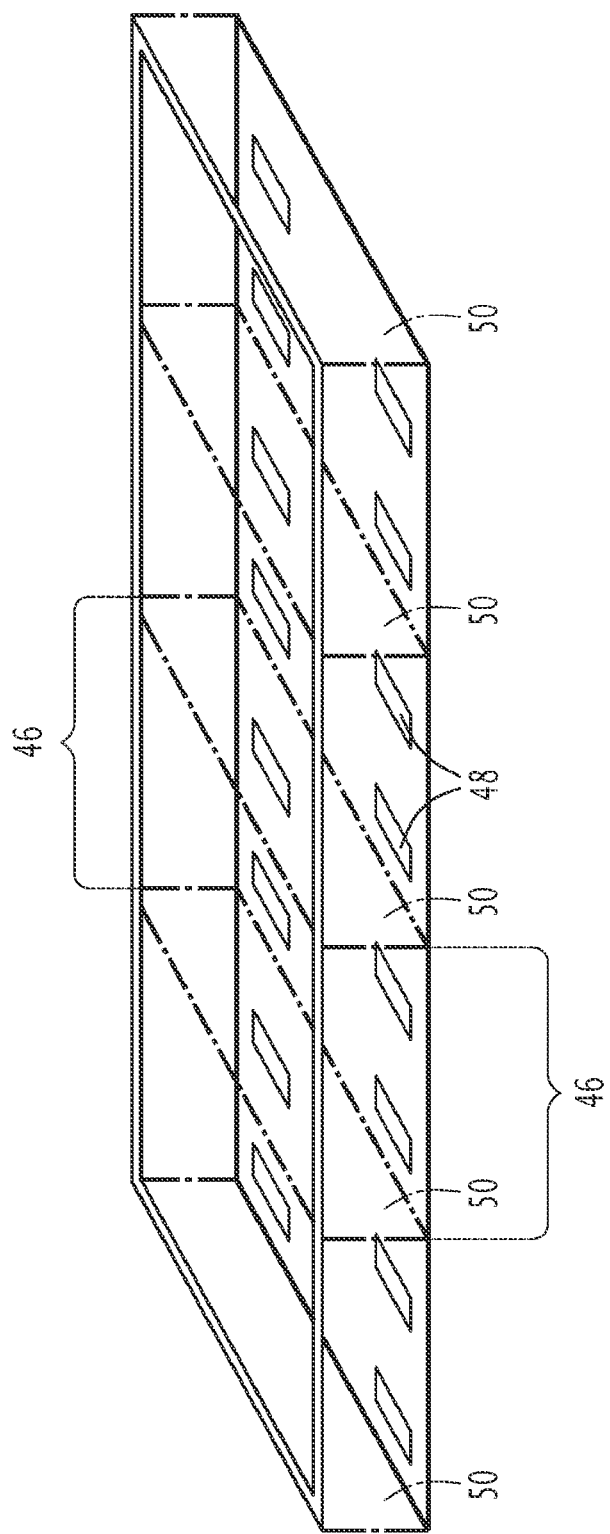
FIGS. 6 and 7 illustrate different variants of an embodiment of the proposed architecture in which the electromagnetic modes capable of being superimposed according to the invention further include cavity modes capable of being excited by adding at least one metal cavity within the multilayer structure according to the present invention.
Figure 7:
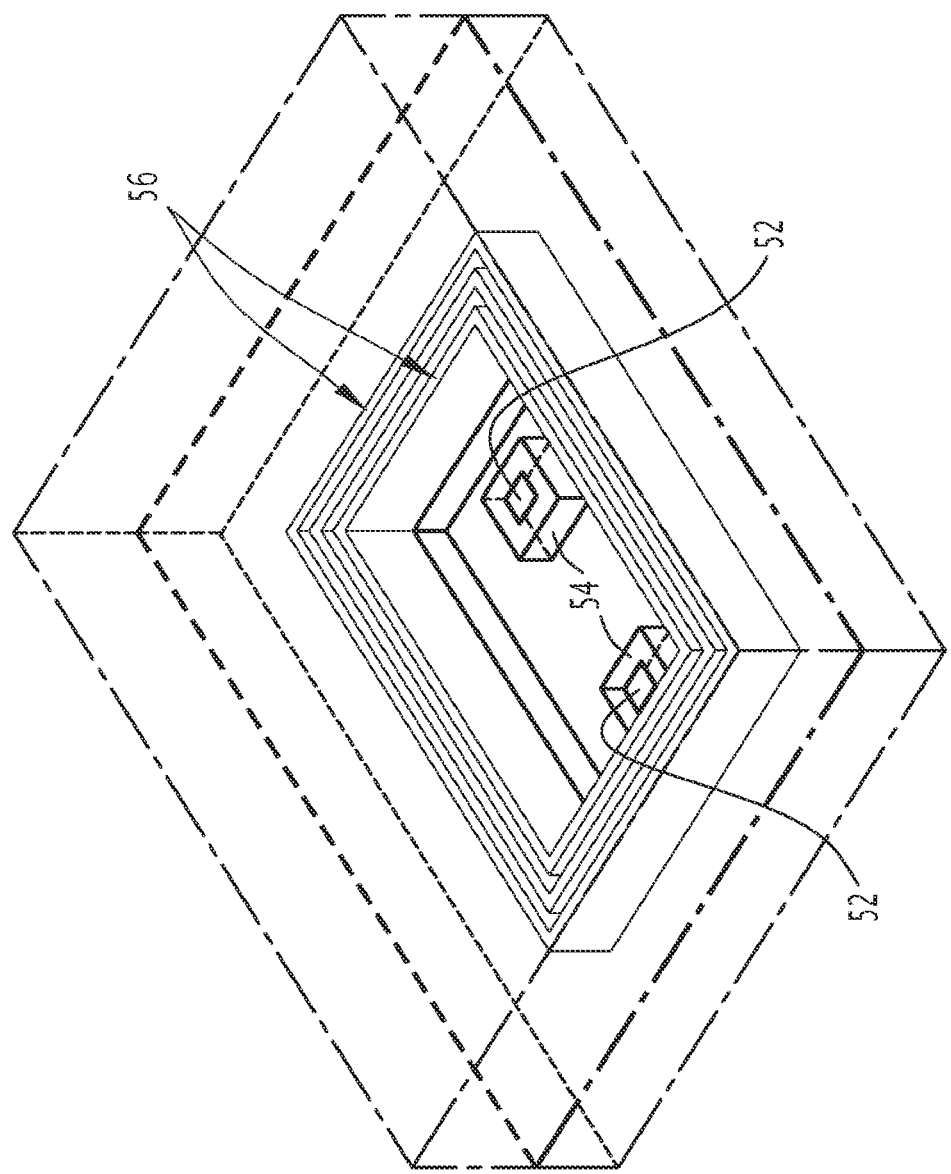

FIGS. 6 and 7 illustrate different variants of an embodiment of the proposed architecture in which the electromagnetic modes capable of being superimposed according to the invention further comprise cavity modes ((i.e., rectangular) capable of being excited by addition of at least one metal cavity within the multilayer structure according to the present invention.

In the solutions/variants proposed previously in relation to FIGS. 1 to 5 for effective illumination of the skin for millimeter wave therapy, the superposition of N cylindrical modes has been proposed, and according to the complementary and optional embodiment of FIGS. 6 and 7, it is also proposed, according to the present invention, to use other types of modes such as cavity modes by using at least one cavity for higher order modes. Depending on the mode, a different excitation must be imposed.

FIG. 6 represents layer 16 of an antenna array consisting of four cavities 46 (of size greater than the λ wavelength). The excitation of the cavities 46 formed by four metal walls is carried out by N slots 48 which make it possible to create a higher order cavity mode. The antenna (formed by the aforementioned layers 16 and 18), loaded by the separation cover 20 with the skin 22, creates a power distribution strictly linked to the order of the cavity mode so created. By configuring beforehand by simulation the cavity modes for each cavity opening 46, it is possible to reduce the coupling between the cavity openings 46 and thus increase the efficiency of the device proposed according to the present invention.

The variants illustrated by FIGS. 1 to 6 present different antenna devices, presenting the stack of FIG. 1, and illuminating the skin 22 with a separating dielectric cover 20. As is known, the power density in the skin 22 is exponentially attenuated, making it essential to concentrate all field components in the penetration.

Leakage waves excited according to variants 1 to 6 exhibit power dissipation in all axes, namely in x, y and z. The component normal to the skin face 22 along the z-axis contributes to skin penetration while the other components can be treated as leakage loss.

Fields which penetrate directly into the skin (energy of the z component of the Poynting vector) can be of the order of half the total power density excited by the source. The other components of the field gradually escape towards the skin or escape through the edges of the plastic covering 20 including the radome.

To remedy this, FIG. 7 illustrates an extension of the antenna devices previously proposed, with a planar radiating element 52 corresponding to a patch (or to the planar radiating elements presented previously $19_A$ and $19_B$) surrounded by a cavity 54, and based on the superposition modes as a semi-finished medium limited by metal walls 56. Indeed, the medium inside the metal walls 56 is capable of creating a cavity of size greater than two guided wavelengths and thus supports higher order modes. These metal walls 56 can in particular be introduced into the fifth covering layer 20 by creating an additional cavity and minimising the effects of leakage.

Such an open cavity formed by the metal walls 56, is likely to lead to mismatching and leakage through the small gap between the cavity and the skin. To avoid these effects, it is proposed to terminate the metal walls 56 of the cavity with studs (i.e., stubs) in adaptation.

As an optional addition, as shown in FIG. 8, the fifth cover layer radome 20 is configured to be a modulated dielectric cover 58 to reduce power leakage through the cover 20 side.

More precisely, it is known to use a grounded modulated dielectric to transform surface waves into leaky waves or to optimize radiation in the far field. According to the present invention, it is specifically proposed to use similar phenomena in the reactive zone between the antenna device and the skin to capture the surface waves created in the dielectric cover and transform them into illumination of the skin.

FIG. 8 shows an array of two planar radiating elements 52 within a cavity 54 loaded with a modulated dielectric 58.

For a classic design of such a modulated surface 58 for a leaky wave antenna device, the radius of the radiating element must be several wavelengths, whereas for a compact application another type of modulation depending on the type of planar radiating element used is applied such as a regular pyramid-shaped pattern for radiating elements corresponding to patch type antennas.

Such a modulated dielectric cover is, according to the present invention, suitable for being considered as an adaptation layer which allows a better concentration of the fields in the reactive zone, and a reduction of the power dissipation escaping by the edges of the coverage is obtained, which improves the reduction of leakage.

Those skilled in the art will understand that the invention is not limited to the embodiments described, nor to the particular examples of the description, the embodiments and the variants mentioned above being suitable for being combined with each other to generate new embodiments of the invention.

The present invention thus proposes a solution for uniform and punctual near-field illumination of the skin. This antenna device is suitable for use in the application of millimeter wave medical therapy, for acupuncture and stimulation of endorphins at 1-100 GHz, for the epidermal detection of cancer, or to increase the capacity of penetration of electromagnetic waves in human tissues or more generally in inhomogeneous media.

The new antenna device architecture is simple to implement thanks to the separation between the upper layers 16, 18 and 20 RF and the lower metal layers of layer 12 allowing a reduction in the mutual coupling between these RF and DC layers, a reduction of loss and therefore of energy consumption.

Furthermore, the use, according to the present invention, of the transition between standing wave(s) and leaky wave(s) does not require a loss power divider.

Finally, the superposition of modes generated by means of the antenna device 10 according to the present invention makes it possible to effectively create a near field with a quasi-uniform or multiple distribution of hot spots.

The superposition of modes as well as the transition between standing wave(s) and leaky wave(s) used according to the present invention have not been used so far for millimeter wave therapy in order to obtain a distribution uniform near-field and multiple hotspots.

The invention claimed is:

1. Antenna device for near-field illumination of the skin by millimeter waves, wherein said device is configured to superimpose a plurality of electromagnetic modes in the near field using a multilayer structure comprising, according to a vertical direction of stacking:
   a first power supply layer comprising at least a first dielectric on an application-specific integrated circuit and on a first lower part of a metallic DC power supply circuit,
   a second DC power supply layer, superimposed on the first power supply layer in the vertical stacking direction, and comprising a second upper part of a metallic DC power supply circuit,
   a third layer, superimposed on the second supply layer in the vertical stacking direction, and comprising a second dielectric on a metal plane,
   a fourth layer comprising at least one planar radiating element of said antenna device, the fourth layer is superimposed on the third layer in the vertical stacking direction, the metal plane of the third layer acts as a ground plane of the radiating element, and
   a fifth layer, superimposed on the fourth layer in the vertical stacking direction, and comprising a radome capable of separating said at least one radiating element from the skin,
   the antenna device further comprising at least one feed line extending vertically from the first layer to the fourth layer.

2. The antenna device according to claim 1, wherein the electromagnetic modes capable of being superimposed are cylindrical modes.

3. The antenna device according to claim 2, wherein the electromagnetic modes capable of being superimposed, further comprise cavity modes capable of being excited by adding at least one metal cavity within the multilayer structure.

4. The antenna device according to claim 1, wherein the said at least one planar radiating element is a fleeing wave radiating element corresponding to at least one patch with annular slot(s), or at least one patch with continuous transverse stubs.

5. The antenna device according to claim 1, wherein the third layer comprises at least one transverse row of metal via(s) defined by the vertical stacking direction and a transverse direction perpendicular to the vertical stacking direction, said at least one transverse row of metal via(s) extending vertically from the metal ground plane of the third layer to the plane of the fourth layer comprising said at least one planar radiating element.

6. The antenna device according to claim 5, wherein the at least one planar radiating element is a fleeing wave radiating element corresponding to at least one patch with annular slot(s), the third layer comprising, on either side of said at least one patch with annular slot(s) at least one transverse row of metal via(s) extending vertically from the metal ground plane to the plane of the fourth layer comprising said at least one patch with annular slot(s), said at least one feed line extending vertically from the centre of the first supply layer to the centre of said at least one patch with annular slot(s).

7. The antenna device according to claim 5, wherein the at least one planar radiating element is a fleeing wave radiating element corresponding to at least one patch with continuous transverse stubs, the third layer comprising, on each side of at least one patch with continuous transverse stubs, at least one transverse row of metal via(s) extending vertically from the metal ground plane to the plane of the fourth layer comprising said at least one patch with continuous transverse stubs, said at least one supply line extending vertically from the centre of the first layer to the centre of the fourth layer comprising said at least one patch with continuous transverse stubs, slots of said at least one patch with continuous transverse stubs being distributed symmetrically on either side of the feed point supplied by the feed line within the fourth layer.

8. The antenna device according to claim 5, wherein the at least one planar radiating element is a fleeing wave radiating element corresponding to at least one patch with continuous transverse stubs, the third layer comprising, located substantially near a first transverse end of said third layer, at least one transverse row of metal via(s) extending vertically from the metallic ground plane to the plane of the fourth layer comprising said at least one patch with continuous transverse stubs, said at least one supply line, extending vertically from the first layer to the fourth layer by being substantially located at a level of a second transverse end, of the third layer, parallel and opposite to the first transverse end of said third layer located substantially close to said at least one transverse row of metal via(s), said at least one supply line being able to excite a first transverse magnetic mode of said at least one patch with continuous transverse stubs.

9. The antenna device according to claim 8, further comprising between said at least one transverse row of metal via(s) and said at least one feed line, at least two other metal vias extending vertically from the metal ground plane to the plane of the fourth layer comprising at least one patch with continuous transverse stubs.

10. The antenna device according to claim 5, wherein the at least one planar radiating element is a fleeing wave radiating element corresponding to at least one patch with continuous transverse stubs, the third layer comprising, located substantially near a first transverse end of said third layer, at least one transverse row of metal via(s) extending vertically from the metallic ground plane to the plane of the fourth layer comprising said at least one patch with continuous transverse stubs, and comprising at least two longitudinal waveguides obtained by inserting within the third layer at least one other longitudinal perpendicular row of metal via(s), in a longitudinal direction, to both said at least one transverse row of metal via(s) and to the metal ground plane, said at least one other longitudinal row of metal via(s) extending vertically from the metallic ground plane to the plane of the fourth layer with at least one patch with continuous transverse stubs.

11. The antenna device according to claim 10, wherein said at least one longitudinal row of metal via(s) extends longitudinally from said at least one transverse row of metal via(s) and beyond the last slot of said at least one patch with continuous transverse stubs while stopping at a distance from a second transverse end, of the third layer, parallel and opposite the first end of this third layer located substantially close to the at least one transverse row of metal via(s), said at least one supply line, extending vertically from the first layer to the fourth layer by being located longitudinally between:
   the end of said at least one longitudinal row of metal via(s) opposite to said at least one transverse row of metal via(s), and
   the second transverse end of the third layer, parallel and opposite to the first transverse end of said third layer located substantially close to said at least one transverse row of metal via(s).

12. The antenna device according to claim 11, wherein said at least one longitudinal row of metal via(s) extends longitudinally from at least one transverse row of metal via(s) and beyond the second transverse end, of the third layer, parallel and opposite to the first transverse end of said third layer located substantially close to said at least one transverse row of metal via(s), the antenna device then comprising at least two supply lines, extending vertically from the first layer to the fourth layer and being located transversely on either side of at least a longitudinal row of metal via(s).

13. An antenna device according to claim 1, wherein the radome is configured to be a modulated dielectric blanket.

* * * * *